(12) United States Patent
Maruyama et al.

(10) Patent No.: US 7,649,016 B2
(45) Date of Patent: Jan. 19, 2010

(54) ANTITUMOR MEDICINE

(75) Inventors: Ikurou Maruyama, Kagoshima (JP); Kazuhiro Abeyama, Kagoshima (JP); Yasushi Yoshimoto, Kagoshima (JP)

(73) Assignee: Nihon Starch Co., Ltd., Kagoshima (JP)

( * ) Notice: Subject to any disclaimer, the term of this patent is extended or adjusted under 35 U.S.C. 154(b) by 0 days.

(21) Appl. No.: 10/577,447

(22) PCT Filed: Oct. 28, 2004

(86) PCT No.: PCT/JP2004/016354

§ 371 (c)(1), (2), (4) Date: Apr. 27, 2006

(87) PCT Pub. No.: WO2005/040147

PCT Pub. Date: May 6, 2005

(65) Prior Publication Data

US 2007/0135517 A1 Jun. 14, 2007

(30) Foreign Application Priority Data

Oct. 28, 2003 (JP) ............................. 2003-366798

(51) Int. Cl.
*A61K 31/365* (2006.01)

(52) U.S. Cl. ..................................................... 514/473

(58) Field of Classification Search ....................... None
See application file for complete search history.

(56) References Cited

U.S. PATENT DOCUMENTS 6,914,175 B2 * 7/2005 Buchter-Larsen et al. 800/317.2

FOREIGN PATENT DOCUMENTS

| JP | 8-59646 | 3/1996 |
| JP | 9-505988 | 6/1997 |
| JP | 2001-89377 | 4/2001 |
| JP | 2003-519660 | 6/2003 |
| WO | 95/10616 | 4/1995 |
| WO | 00/56838 | 9/2000 |
| WO | 01/51058 | 7/2001 |
| WO | 01/51480 | 7/2001 |
| WO | 02/26060 | 4/2002 |
| WO | 02/26061 | 4/2002 |
| WO | 03/038084 | 5/2003 |
| WO | 03/038085 | 5/2003 |
| WO | 03/038107 | 5/2003 |
| WO | WO 03038107 A2 * | 5/2003 |

OTHER PUBLICATIONS

NCI—Antioxidants and Cancer Prevention: Fact Sheet. Jan. 8, 2003 http://www.cancer.gov/cancertopics/factsheet/antioxidantsprevention/print?page=&keyword=.*
Behrend et al. (Biochemical Society Transaction, 2003, vol. 31, part 6, pp. 1441-1444).*
Vieira et al. (British Journal of Pharmacology, 1998, vol. 123, pp. 565-573).*
Yamaji et al. (Planta Med 2002, vol. 68, pp. 16-19).*
Baute, M. A., et al., "Enzymic Activity Degrading 1,4-α-D-Glucans to Ascopyrones P and T in Pezizales and Tuberales," *Phytochemistry*, vol. 33, No. 1, (1993), p. 41-45.
Shafizadeh, F., et al., "1,5-anhydro-4-deoxy-D-*glycero*-hex-1-en-3-ulose and Other Pyrolysis Products of Cellulose," *Carbohydrate Research*, vol. 67, (1978), p. 433-447.
Stevenson, T. T., et al., "The Crystal Structure of 1,5-anhydro-4-deoxy-D-*glycero*-hex-1-en-3-ulose," *Carbohydrate Research*, vol. 90, (1981), p. 319-325.
European Patent Office Search Report issued in counterpart European Application No. 04 79 3334.
Baute M.A. et al., "*Les Ascopyrones P et T: Deux Nouveux Composés Issus du Métabolisme d'Ascomycètes Activés*", ARS Pharamceutia, Granada, Spain, vol. 33, No. 1-4 part I, Jan. 1, 1992, pp. 440-446.

* cited by examiner

*Primary Examiner*—Janet L. Epps-Smith
(74) *Attorney, Agent, or Firm*—Wenderoth, Lind & Ponack, L.L.P.

(57) ABSTRACT

There is provided an antitumor medicine comprising 1,5-D-anhydrofructose and/or ascopyrone. The antitumor medicine has effects of ascopyrone in inhibiting the growth and metastasis of tumors, is expected to inhibit inflammation and exerts an excellent effect on prognosis.

1 Claim, 11 Drawing Sheets

ANTITUMOR MEDICINE

TECHNICAL FIELD

The present invention relates to an antitumor medicine comprising 1,5-D-anhydrofructose and/or ascopyrone as active ingredient(s).

BACKGROUND ART 1,5-D-anhydrofructose (hereinafter may be abbreviated as "1,5-AF") can be produced by using α-1,4-glucan lyase which is an enzyme contained in a certain kind of ascomycete or red alga and using starch or decomposed starch as a substrate. 1,5-D-anhydrofructose has an interesting, peculiar structure, dehydrated form of glucose. It has already been reported that 1,5-AF has antioxidative activity (refer to JP-A 9-505988 (the term "JP-A" as used herein means an "unexamined published Japanese patent application")) and antimicrobial activity (refer to JP-A 2001-89377). Further, it has been reported in recent studies that 1,5-AF also has an antihyperglycemic effect (refer to JP-A 2003-519660). It has been receiving attention as novel sugar having bioactivity.

Meanwhile, it has been reported that ascopyrone can be prepared from an enzyme reaction of 1,5-D-anhydrofructose (refer to WO03/38084, WO03/38085 and WO03/38107). It has been known that ascopyrone is biosynthesized by a certain kind of ascomycete (refer to M. A. Baute., phytochemistry, 33, (1991) 41-45). It has been reported that ascopyrone can also be prepared by causing a fungi extract of Pezizales orders such as *Picaria leiocarpa* and *Anthracobia melaloma* and Tuberales orders such as *Tuber melanosporum* to act on 1,5-D-anhydrofructose.

Ascopyrone P (2-hydroxymethyl-5-hydroxy-2,3-dihydro-4H-pyran-4-one) was prepared by a group of U.S. scientists in 1978 and 1981 by thermally decomposing amylopectin, amylose and cellulose for the purpose of using ascopyrone P as a staring material for organic synthesis (refer to Shafizadeh, F., et al., Carbohydr. Res., 67, (1978) 433 to 447 and Stevenson, F., et al., Carbohydr. Res., 90, (1981) 319 to 325).

It has been reported that as in the case of 1,5-D-anhydrofructose, ascopyrone P (hereinafter may be abbreviated as "APP") also has antioxidative activity and antimicrobial activity (refer to WO02/26060, WO02/26061 and WO00/56838).

Most of antitumor medicines used in clinics at present have a pro-oxidant effect according to their chemical nature and have a high possibility of causing a side effect such as hepatopathy, nephropathy, bone marrow suppression or pneumonopathy. In contrast, 1,5-D-anhydrofructose and ascopyrone have antioxidative activity and also inhibit activation of inflammatory cells. It is assumed that they thereby attenuate such inflammatory tissue damage as seen in antitumor medicines such as bleomycin and cisplatin. Accordingly, by use of the antitumor medicine of the present invention in combination with other antitumor medicines, not only enhancement of antitumor effect but also application to a chemotherapy aid which alleviates side effects can be expected.

DISCLOSURE OF THE INVENTION

An object of the present invention is to provide use of 1,5-D-anhydrofructose and/or ascopyrone for inhibiting the growth and metastasis of tumors.

Another object of the present invention is to provide an antitumor medicine with excellent prognosis which comprises 1,5-D-anhydrofructose and/or ascopyrone as active ingredient(s) and is expected to inhibit inflammation.

Other objects and advantages of the present invention will become apparent from the following descriptions.

According to the present invention, the above objects and advantages of the present invention are achieved by an antitumor medicine comprising 1,5-D-anhydrofructose and/or ascopyrone.

In the present invention, "antitumor" is a notion including an effect of inhibiting the growth and metastasis of tumors.

That is, when an appropriate amount of the medicine of the present invention is given to a living body having tumor cells in accordance with a proper method, the growth and metastasis of tumors can be inhibited significantly.

Illustrative examples of ascopyrone in the present invention include a dehydration product of 1,5-D-anhydrofructose resulting from dehydration of 1,5-D-anhydrofructose by 1,5-D-anhydrofructose dehydratases derived from ascomycetes and a dehydration product of 1,5-D-anhydrofructose produced by a chemical or physical operation, e.g., treating 1,5-D-anhydrofructose under alkali conditions or subjecting 1,5-D-anhydrofructose to a heat treatment. Exemplary structural formulas of ascopyrone are shown in FIG. 1.

The present medicine can be administered in accordance with various methods known per se. Its dose, administration site, dosing interval, dosing period and the like can be determined in consideration of the age, body weight and condition of a patient or other medicines or treatments which may be used in combination with the present medicine.

A method of administering the present medicine is not particularly limited. For example, it can be administered intravenously, hypodermically or intraperitoneally by injection, drip or the like or orally.

Further, it is also possible to incorporate the present medicine into a food and causing a patient to ingest the food.

Its dose varies according to an administration method, a dosing interval, the kind of tumor and the severity of the condition of a patient. For example, the dose of ascopyrone for one treatment may be 0.000001 μg/kg to 1,000 mg/kg, preferably 0.001 μg/kg to 500 mg/kg, and the dose of 1,5-D-anhydrofructose for one treatment may be 0.001 μg/kg to 10,000 mg/kg, preferably 0.01 mg/kg to 1,000 mg/kg.

Further, it is also possible to divide the dose for one treatment into several doses and administer them.

The form of the medicine of the present invention is not particularly limited. Illustrative examples thereof include a tablet, capsule, powdered medicine, granule, suppository, injection, and transdermal absorbent. Further, the medicine of the present invention may contain components required to prepare a preparation, e.g., a preparation carrier, a vehicle and a stabilizer. In addition, the medicine of the present invention may also contain other antitumor medicines or other pharmacological components or nutritional components such as glucose as long as it can exert the effect of the present invention.

Hereinafter, the results of examining the present invention will be described in detail. In the following test, 1,5-D-anhydrofructose and ascopyrone which had been prepared in accordance with known methods were used.

TEST EXAMPLE

Cell Lines and Culture Methods

Adhesion cancer cell lines C57 BL/6 mouse melanoma cell lines (B16 melanoma), human lung adenocarcinoma cell lines (A549), human keratinocyte derived tumor-like cell lines (HaCaT) and human cervical cancer cell lines (Hela) were cultured at 37° C. and a $CO_2$ concentration of 5% in DMEM media having 10% FCS (fetal calf serum) and 2% penicillin/streptomycin added thereto. Floating tumor cells THP-1 (promyelocytic leukemia cell lines) were cultured at 37° C. and a $CO_2$ concentration of 5% in an RPMI 1640 medium containing 10% FCS and 2% penicillin/streptomycin.

Method for Measuring the Number of Living Cells

After B16 melanoma cells having multiplied on a 6-well plate were fixed by 2% glutaraldehyde, they were stained with 4% crystal violet, and stainable cells were determined to be living cells.

Cell Death Percentage and Method for Measuring the Proportion of Cells in Each Cell Cycle The cell culture media were stimulated by ascopyrone P solutions (prepared by dissolving ascopyrone P in dimethyl sulfoxide (DMSO)) of various concentrations and cultured for a predetermined time. Thereafter, cells were collected in a floating state by use of trypsin. Then, the cells were fixed by 70% ethanol at 4° C. for 30 minutes and then stained with a 50 μg/ml propidium iodine (PI) solution. After 30 minutes, DNA histograms were prepared by use of an FACS to examine cell death percentages and cell cycles.

Method for Measuring the Number of Adhered Cells

A 1,5-D-anhydrofructose solution (prepared by dissolving 1,5-D-anhydrofructose in DMSO) was added to the THP-1 cell culture medium, and the resulting medium was then stimulated by phorbol ester (PMA; phorbol myristate acetate). After the medium was cultured at 37° C. and a $CO_2$ concentration of 5% for one hour, adhered cells were stained with a Giemsa staining method.

Results and Considerations

1) Effect of Inhibiting Cell Growth by Ascopyrone P $5 \times 10^3$ cells/ml of B16 melanoma cells (C57 BL/6 mouse melanoma cells) were disseminated into a 6-well plate. After the cells were attached to the bottom face (24 hours), an ascopyrone P solution (using DMSO as a solvent) was added in equal amounts to achieve a final concentration of 0 to 0.70 mM in the culture solutions. After the cells were cultured at 37° C. and a $CO_2$ concentration of 5% for one week, the number of living cells was counted.

The results are shown in FIG. 2. When living cells by control (addition of DMSO only) were 100%, the number of living cells was significantly decreased concentration-dependently by addition of ascopyrone P, and the percentage thereof was decreased to 50% or less at the final concentration (0.70 mM). It is assumed from these results that ascopyrone P has an effect of inhibiting the growth of tumor cells.

2) Effect of Inducing Apoptosis of Tumor Cells by Ascopyrone P

It was examined whether the mechanism of an effect of inhibiting the growth of tumor cells by ascopyrone P on B16 melanoma cells was comparable to that of a cell killing effect as is seen in other antitumor medicines. In the examination, in addition to the B16 melanoma cells, 4 types of human cancer cell lines (THP-1: promyelocytic leukemia, HeLa: cervical cancer, A549: alveolar cell carcinoma, HaCaT: cutaneous cancer model cells) were examined for the proportion of dead cells induced by stimulation of ascopyrone P. To the cancer cell culture solutions, ascopyrone P was added to 1.4 mM, and the percentages of dead cells after 48 hours were determined. The results are shown in Table 1.

TABLE 1

| Cancer cells | Percentage of Dead Cells (%) |
|---|---|
| THP-1 (Promyelocytic Leukemia Cells) | 33.3 ± 0.7 |
| HeLa (Human Cervical Cancer Cells) | 8.3 ± 2.0 |
| A549 (Human Alveolar Cell Carcinoma) | 48.6 ± 3.8 |
| HaCaT (Human Keratinocyte Derived Tumor-Like Cells) | 27.2 ± 3.1 |
| B16 Melanoma (C57 BL/6 Mouse Melanoma Cells) | 31.9 ± 3.6 |

It is understood from Table 1 that ascopyrone P shows a cell killing effect having a wide spectrum regardless of the types of cancers derived from the cancer cells. Further, in the experimental system using the HaCaT cells, apoptosis-specific DNA fragmentation was observed in 48 hours after addition of ascopyrone P (1.4 mM) (FIG. 3). Thus, it was confirmed that cell death by ascopyrone P was apoptosis, and the same result was also obtained in the system using the A549 cells. Further, it was observed in the system using the THP-1 cells that ascopyrone P induced cell death within 48 hours at 0.35 mM (FIG. 4).

3) Effect of Inducing Specific Cell Death by Ascopyrone P

It is known that although HaCaT cells have characteristics of tumor cells in the presence of 10% FCS, they have characteristics close to those of normal cells in the presence of low-concentration FCS (1% or lower). By taking advantage of this characteristic, the influence of ascopyrone P on normal cells was examined. The results are shown in FIG. 5. While ascopyrone P induced about 30% of cell death within 48 hours after addition thereof (1.4 mM) in the presence of FCS10% in which the cells grew like tumors (FIG. 5(c)), almost no cell death was observed even in the presence of 1.4 mM of ascopyrone P in the presence of FCS1% in which the cells have characteristics similar to those of normal cells (FIG. 5(b)). Thus, it was indicated that ascopyrone P specifically acted on cells with a high growth rate (tumor cells) and exerted almost no influence on cells with a low growth rate (normal cells).

Meanwhile, for HeLa cells which grew like tumor cells in the presence of FCS10%, a significant increase in S-period cell population and a significant decrease in G2/M period cell population were observed in 24 hours after addition of ascopyrone P (1.4 mM) (FIG. 6), and ascopyrone P induced about 10% of cell death in 48 hours after the addition thereof as described above. Thereby, it is indicated that the point of action of ascopyrone P on the cell cycle is the S period which is a DNA synthetic period and ascopyrone P inhibits transition to the G2/M period and consequently induces cell death. Therefore, when ascopyrone P is given to a living body as an antitumor medicine, it is expected that it specifically exerts a cell killing effect only on tumor cells without affecting normal cells most of which are conceived in the G0/1 period of the cell cycle.

4) Effect of Controlling Function of Integrin by 1,5-D-anhydrofructose

It is known that when leukemia cell lines are stimulated by phorbol ester (PMA), activation of adhesion molecule integrin is observed, and as a result, production of active oxygen, enhancement of cell adhesion and cell infiltration are induced as cell phenomena. Thus, THP-1 cell lines were cultured in the presence of 1,5-D-anhydrofructose, and the function of integrin was evaluated by use of the number of adherent cells after stimulation of the lines by phorbol ester as an index.

The results are shown in FIG. 7. 12.3 mM of 1,5-D-anhydrofructose controlled cell adhesion by phorbol ester to about 25%. Thus, it was inferred that 1,5-D-anhydrofructose could control the function of integrin molecules which are considered to serve an important role in metastasis of tumor cells.

EFFECT OF THE INVENTION

Use of 1,5-D-anhydrofructose and/or ascopyrone can inhibit the growth and metastasis of tumors with almost no side effects.

BEST MODE FOR CARRYING OUT THE INVENTION

Hereinafter, the present invention will be further described with reference to Examples. The present invention shall not be limited by these Examples in any way.

EXAMPLES

Example 1

B16 melanoma cells ($5 \times 10^6$ cells) were disseminated in the abdominal cavities of C57 BL/6 mice, PBS (phosphate buffer) and an ascopyrone P solution were then administered (dosage: 200 mg/kg) into the abdominal cavities every day from the 15th day, and the survival rates were examined (cancerous peritonitis model). It was confirmed that, in this experimental system, when the B16 melanoma cells were disseminated in the abdominal cavities of the mice in advance, the mice died from the 14th day or later when nothing or PBS was applied. The results of examining the life extending effect of ascopyrone P on terminal cancer models by use of the present experimental system are shown in FIG. 8. The average survival days are 8 days for those given ascopyrone P and 4 days for those given PBS, whereby it was confirmed that ascopyrone P had an antitumor effect even in vivo. Further, 40% (n=2) of those given ascopyrone P showed 3 times or longer life time expansion after administration of ascopyrone P than that of controls (those given PBS). This indicates the antitumor effect in vivo of ascopyrone P.

Example 2

As in Example 1, B16 melanoma cells ($5 \times 10^6$ cells) were disseminated in the abdominal cavities of C57 BL/6 mice, and PBS and 1,5-D-anhydrofructose were administered (dosage: 200 mg/kg) into the abdominal cavities every day from the 2nd day. The survival rates are shown in FIG. 9. The average survival days after the tumor cells were disseminated were 19 days for those given 1,5-D-anhydrofructose and 14 days for those given PBS as controls. From these results, the life extending effect of 1,5-D-anhydrofructose on tumor-bearing mice was confirmed.

Example 3

Next, B16 melanoma cells ($1 \times 10^5$ cells) were subcutaneously disseminated in the backs of C57 BL/6 mice, PBS and ascopyrone P were subcutaneously injected into tumor spots (using a solution of ascopyrone P dissolved in PBS in a dosage of 25 mg/kg) every other day from the 3rd day to the 13th day, and the antitumor effects were evaluated based on the volumes (long diameter×short diameter$^2$×0.52) of the tumors (FIG. 10). It was confirmed that although no difference was seen between those given ascopyrone P and those given PBS in terms of the tumor volume until the 7th day after dissemination of the tumor cells, those given ascopyrone P showed a significantly smaller tumor volume than those given PBS from the 7th day and later. In general, it is said in clinical practice that an antitumor medicine with a lower tumor growing rate provides better prognosis. That is, it indicates the antitumor effect in vivo of ascopyrone P. Further, metastasis of tumors was hardly observed when those given ascopyrone P were killed, dissected and observed.

Example 4

Cell culture solutions of promyelocytic leukemia cells (THP-1 cells) were stimulated by an ascopyrone P solution (solution of ascopyrone P dissolved in DMSO), cisplatin solution (solution of cisplatin dissolved in DMSO) and mixed solution of ascopyrone P and cisplatin of various concentrations, and after cultured for 48 hours, suspensions comprising uniform single cells were recovered by sufficient pipetting. Then, some of the suspensions were observed under a microscope to measure the number of cells by use of a hemocytometer. The remaining cell suspensions were fixed by 70% ethanol at 4° C. for 30 minutes and then dyed with final 50 μg/ml of propidium iodine (PI) solution. After 30 minutes, a DNA histogram was prepared by use of FACS, the percentages of cell deaths were checked, and the numbers of living cells were calculated (FIG. 11). When the living cells by control (addition of only DMSO) were 100%, the percentage thereof was decreased to about 30% to about 50% by addition of ascopyrone P, whereby a cell growth inhibiting effect was confirmed. Meanwhile, the percentages of living cells in those given cisplatin and ascopyrone P were about 10%, whereby the synergistic effect of ascopyrone P and cisplatin was confirmed.

Figure 1:
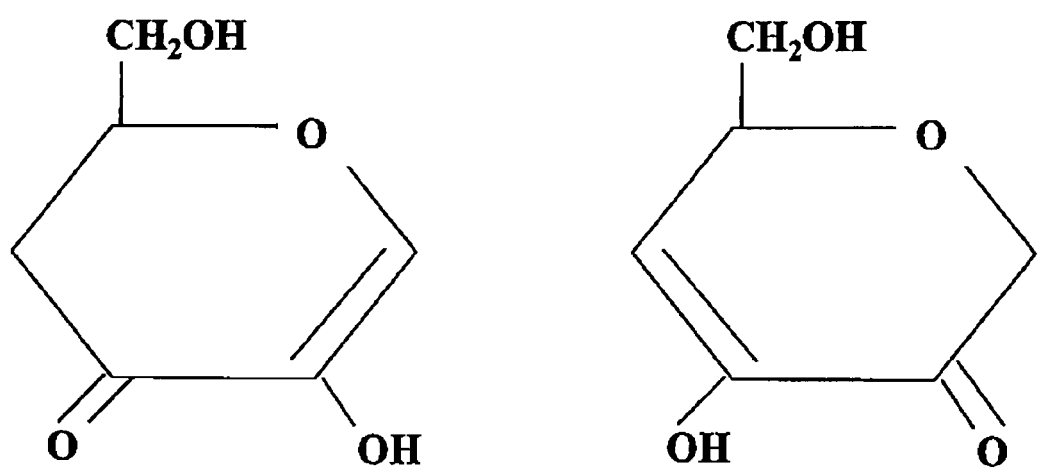
FIG. 1 shows an example of the structural formula of ascopyrone.
Figure 2:
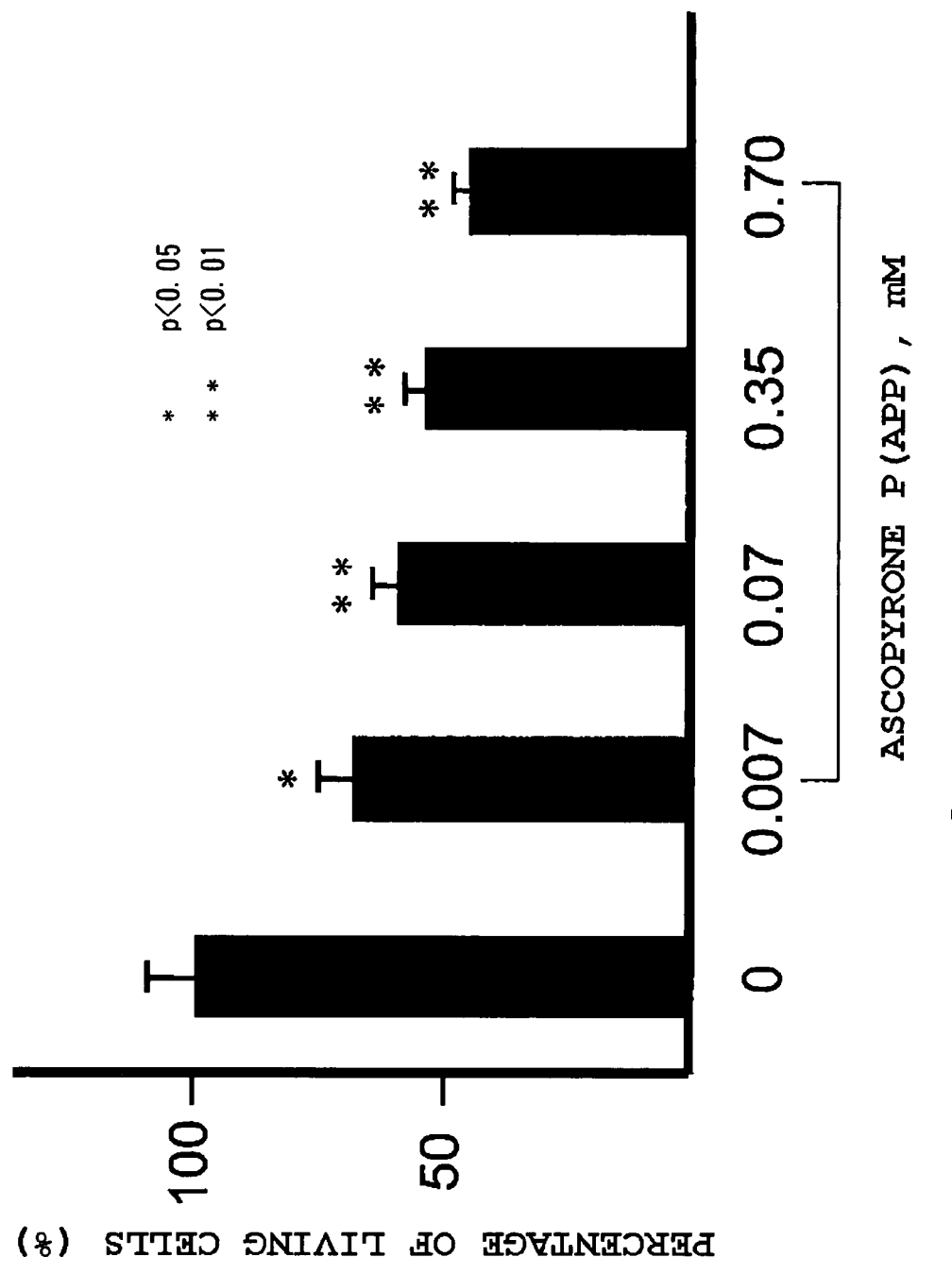
FIG. 2 shows the results of evaluating the effect of inhibiting the growth of cells by ascopyrone P by a crystal violet staining method.
Figure 3:
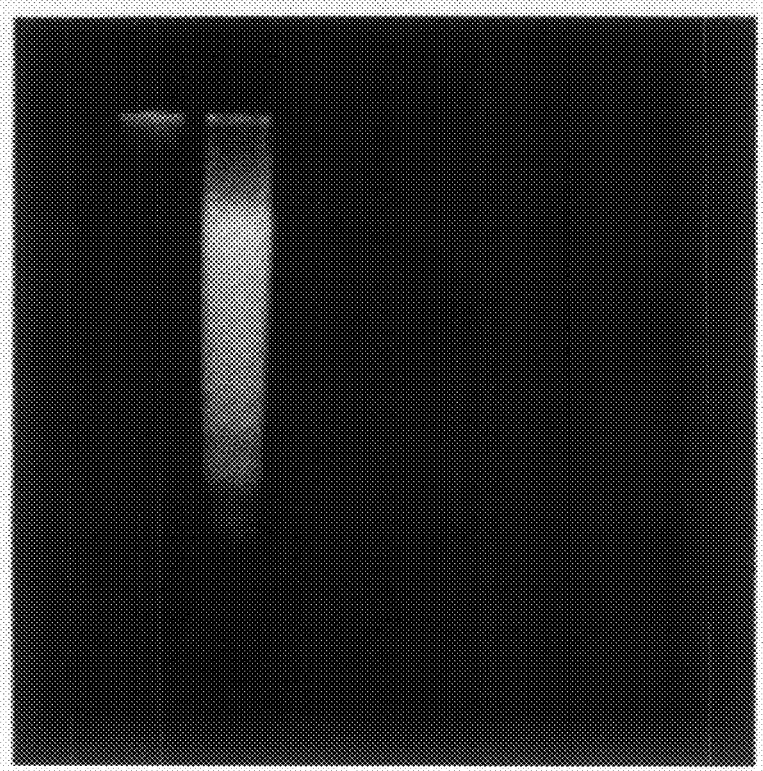
FIG. 3 shows the results of analyzing DNA fragmentation by agarose gel electrophoresis.
Figure 4:
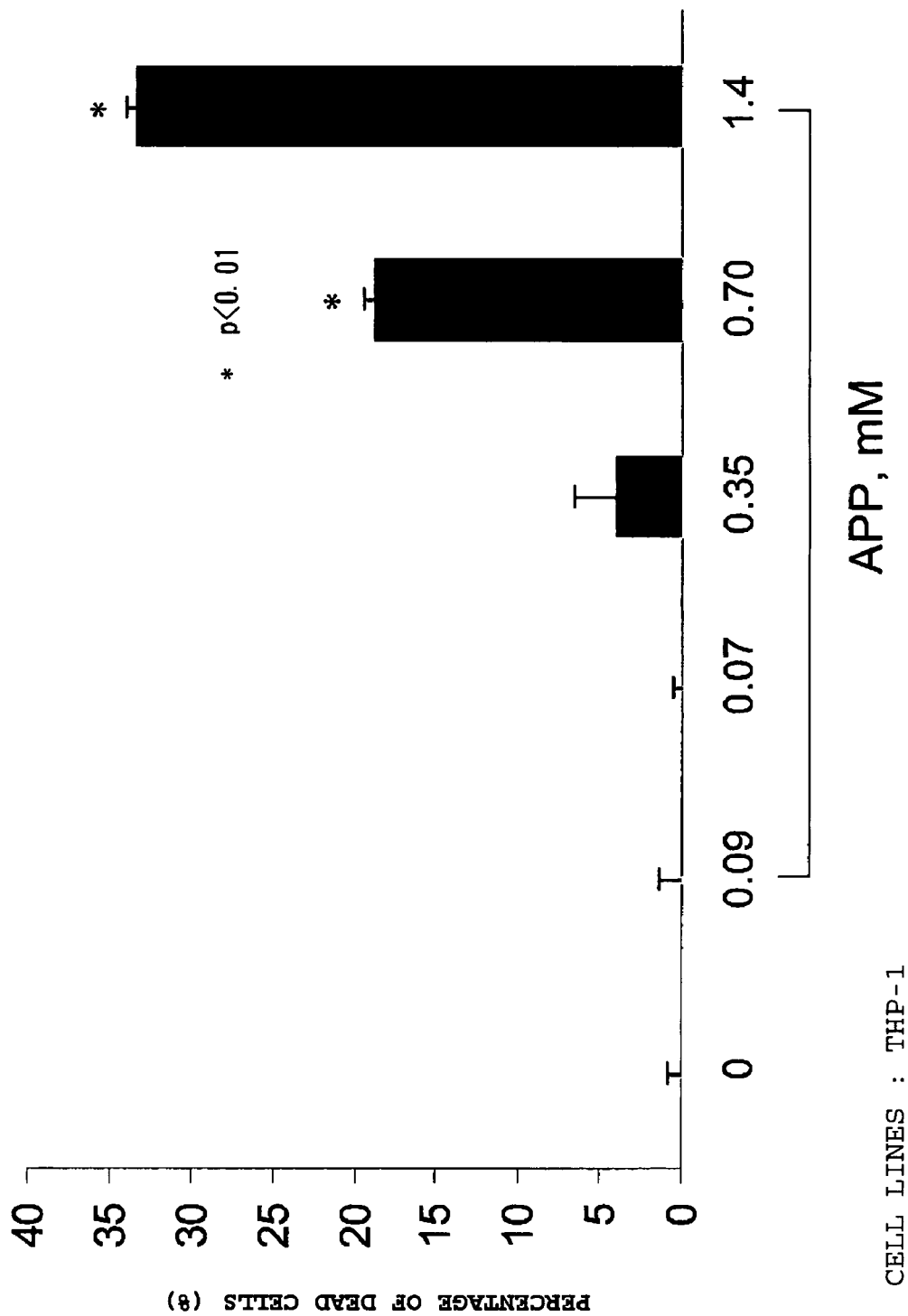
FIG. 4 shows the results of quantitative evaluation of dead cells by flow cytometry (FACS).
Figure 5:
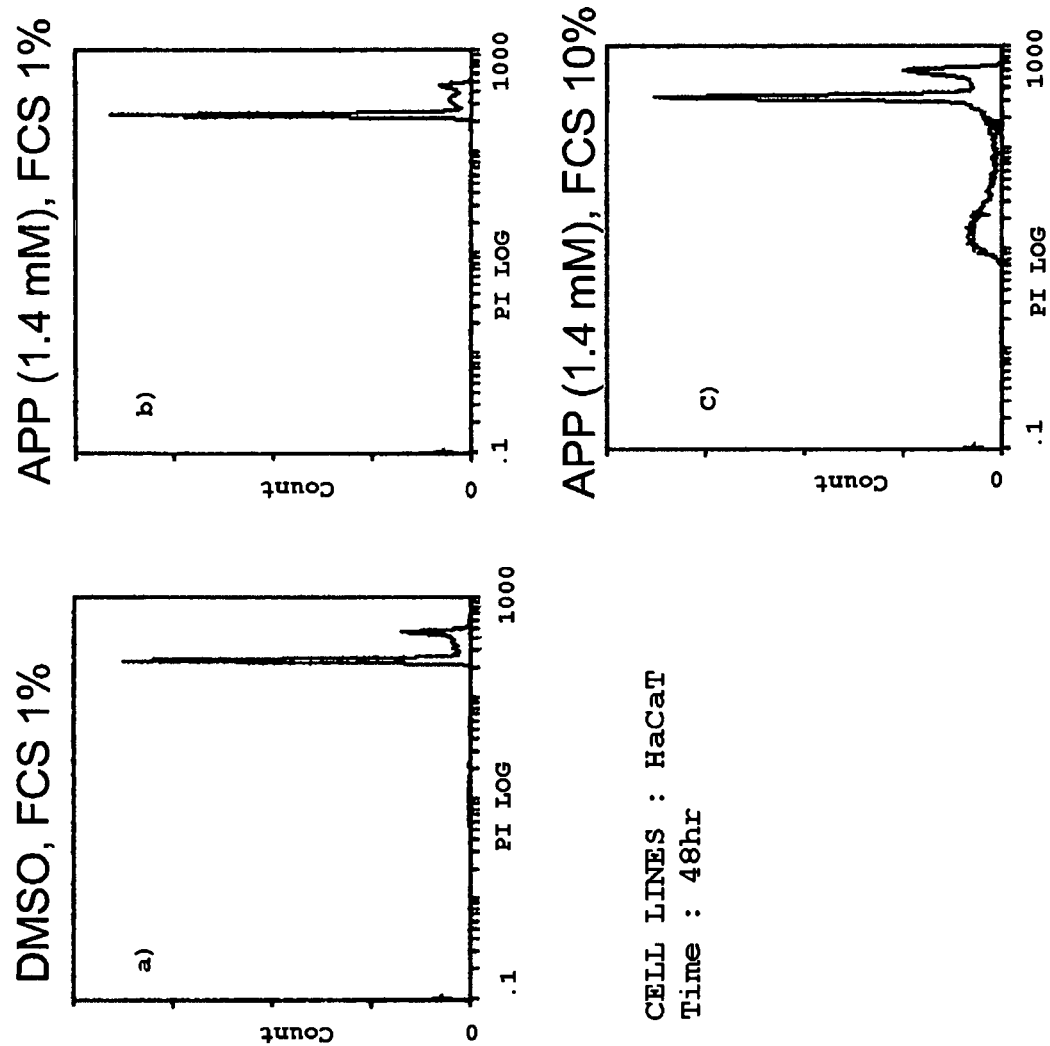
FIG. 5 shows the results of quantitative evaluation of dead cells by flow cytometry (FACS).
Figure 6:
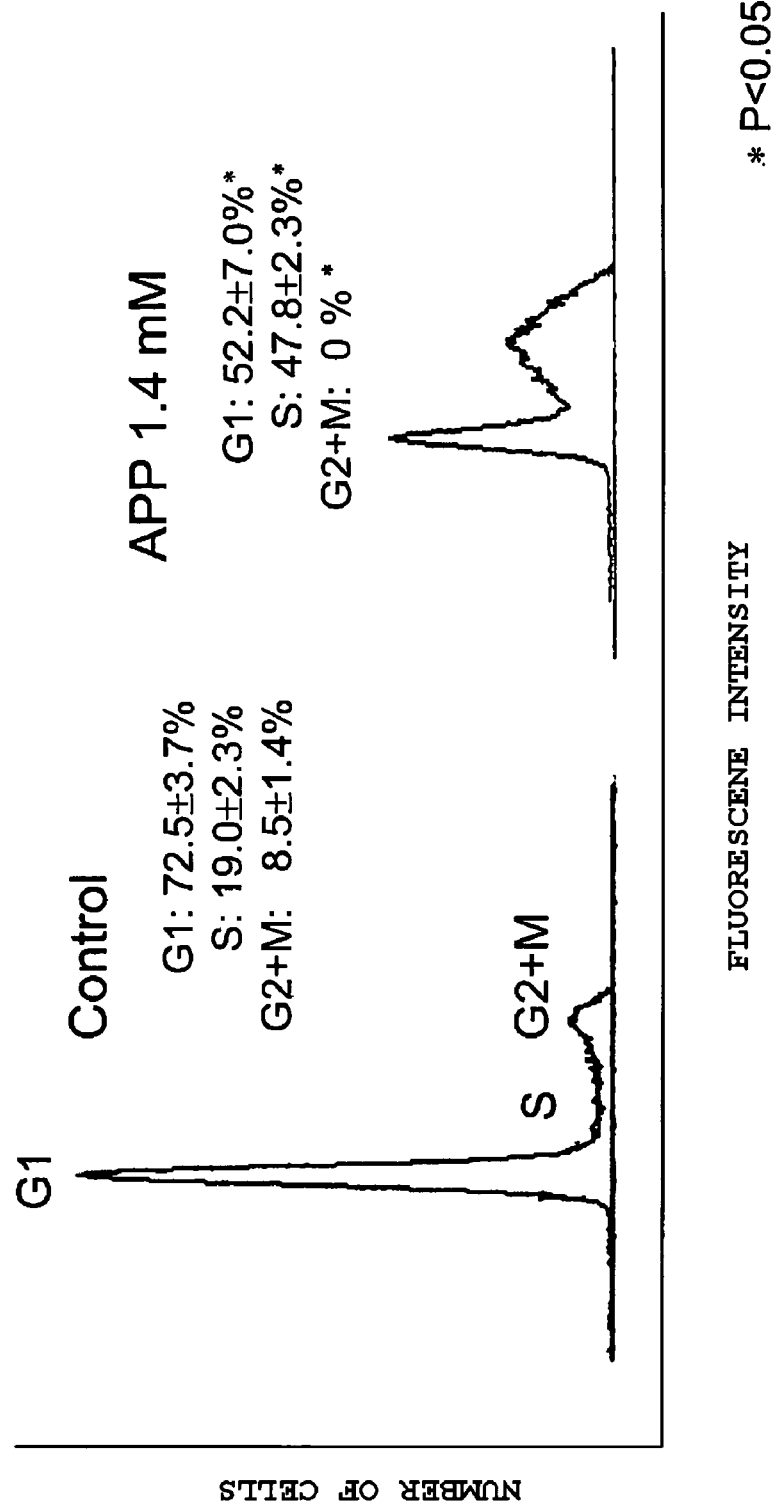
FIG. 6 shows the results of evaluation of the cell cycle by flow cytometry (FACS).
Figure 7:
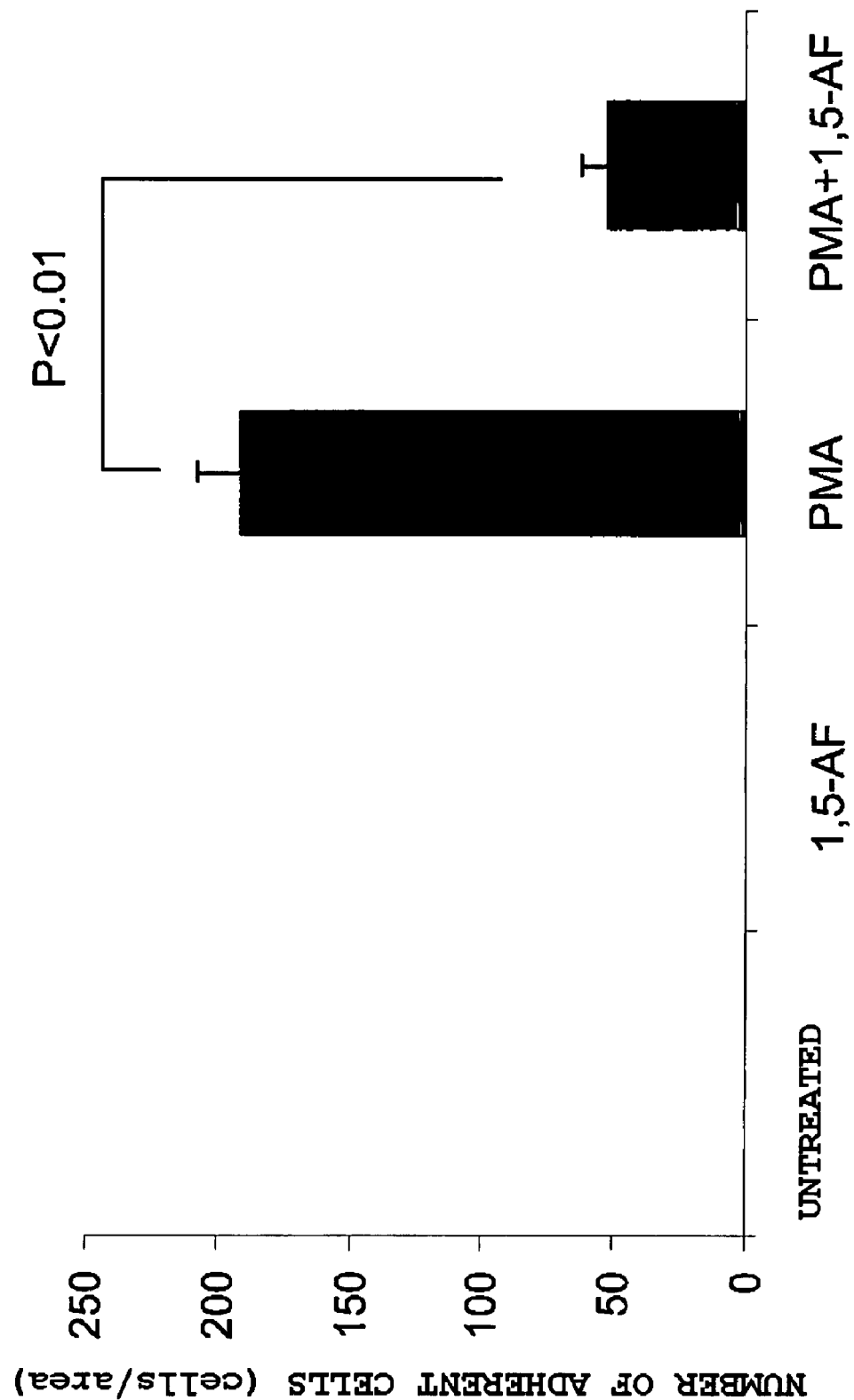
FIG. 7 shows the results of evaluation of the function of integrin in leukemia cell lines.
Figure 8:
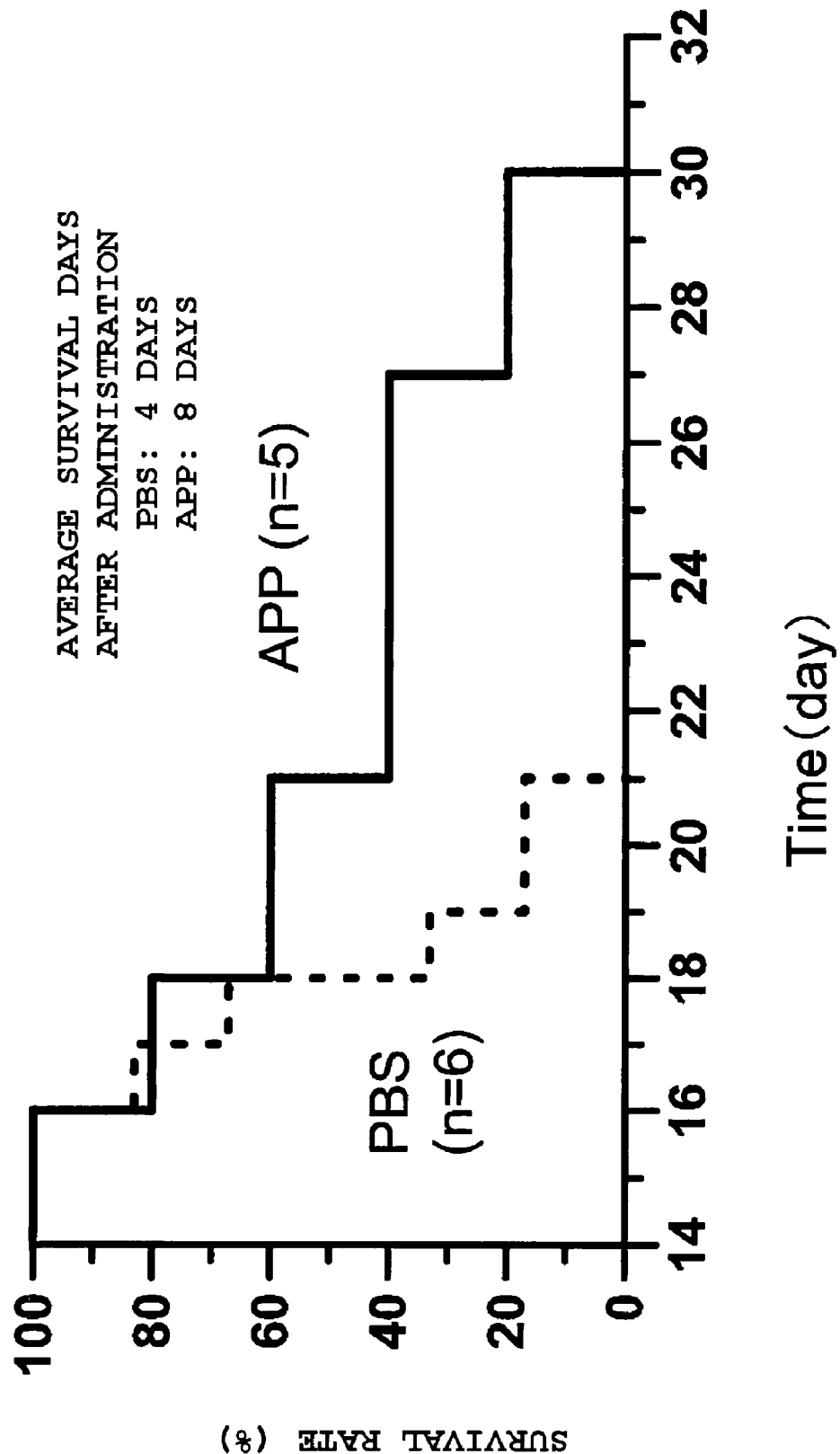
FIG. 8 shows the survival rate of mice after administration of ascopyrone P (Example 1).
Figure 9:
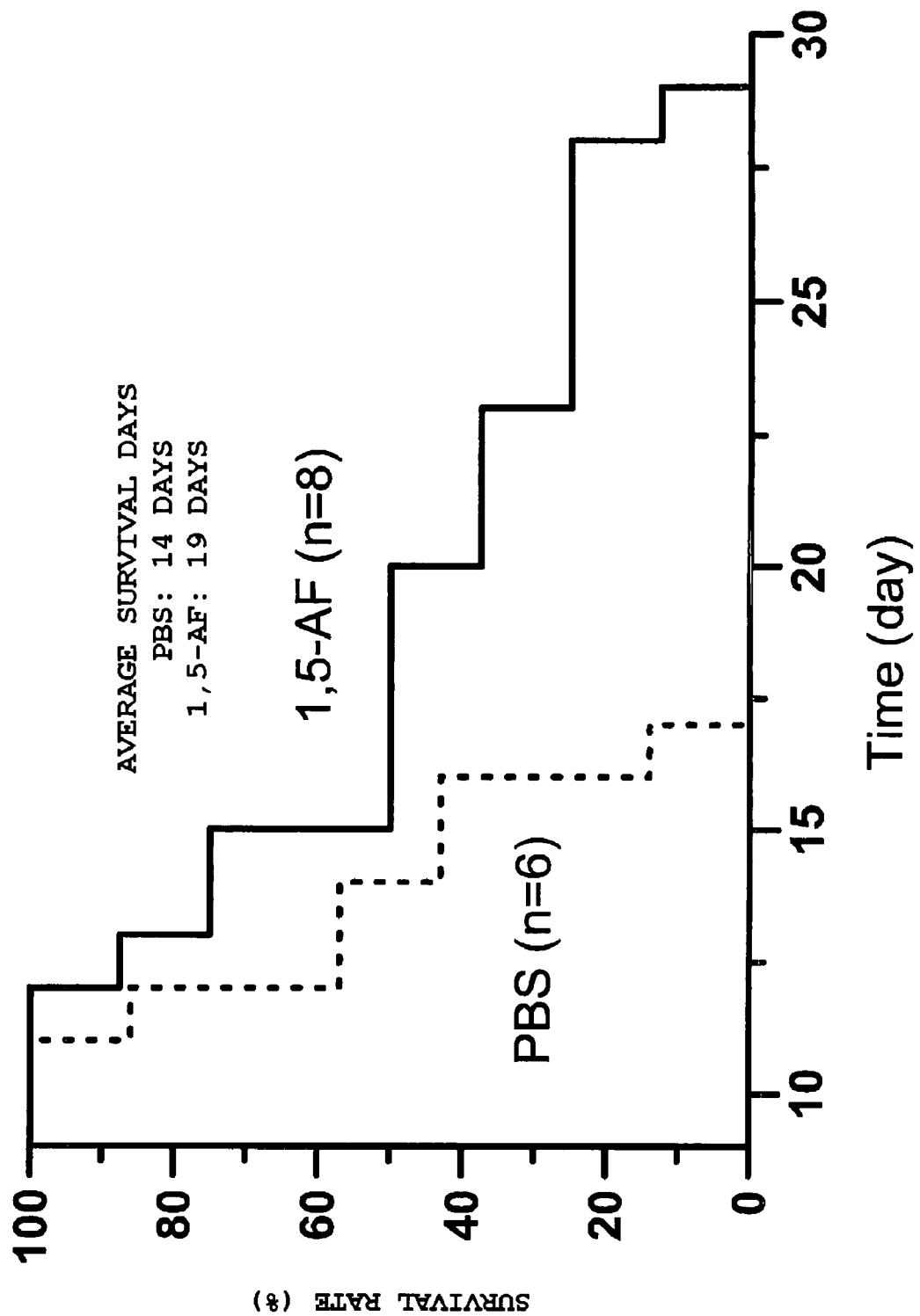
FIG. 9 shows the survival rate of mice after administration of 1,5-D-anhydrofructose (Example 2).
Figure 10:
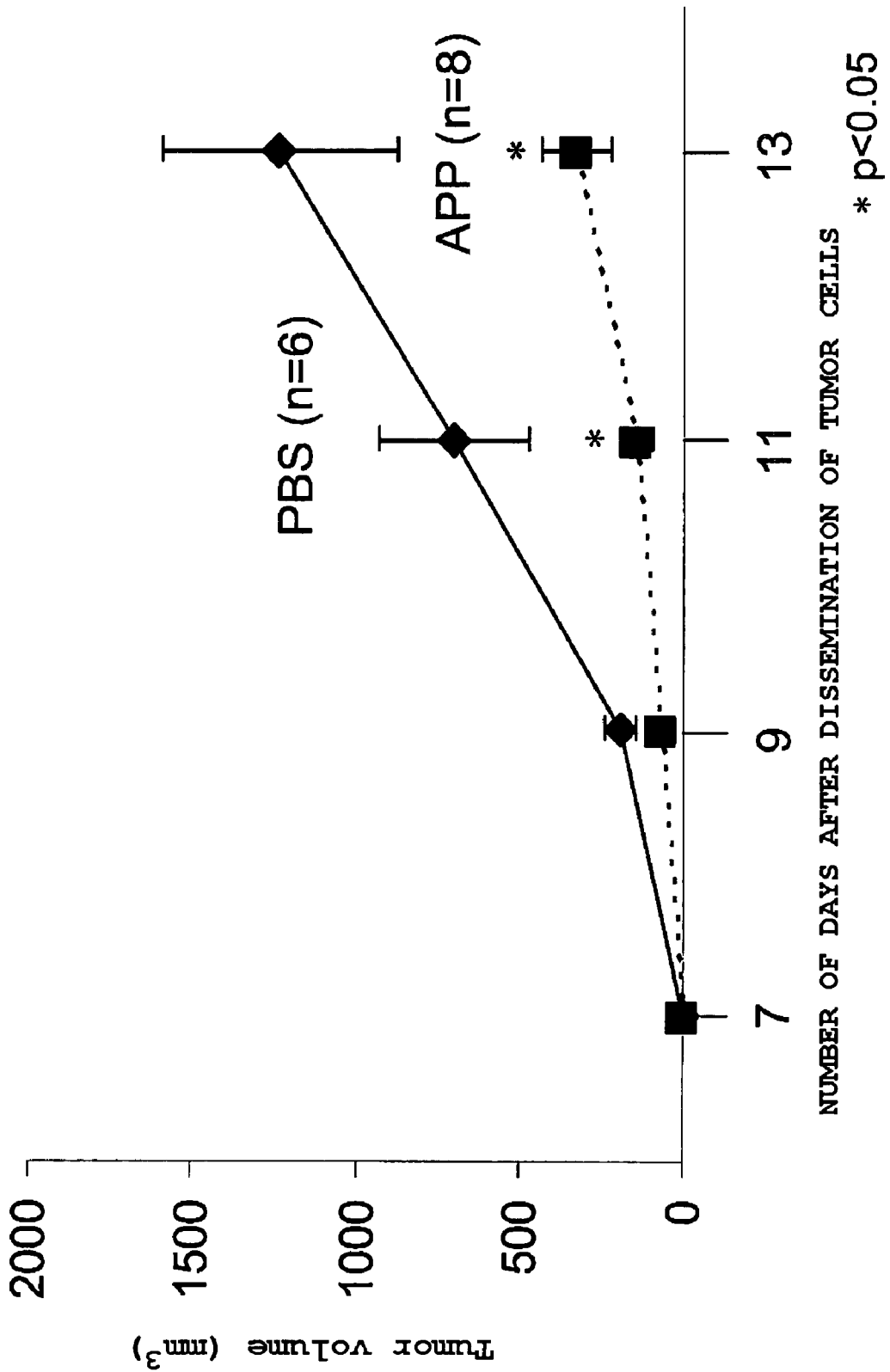
FIG. 10 shows the results of evaluation of the tumor volumes of mice after administration of ascopyrone P (Example 3).
Figure 11:
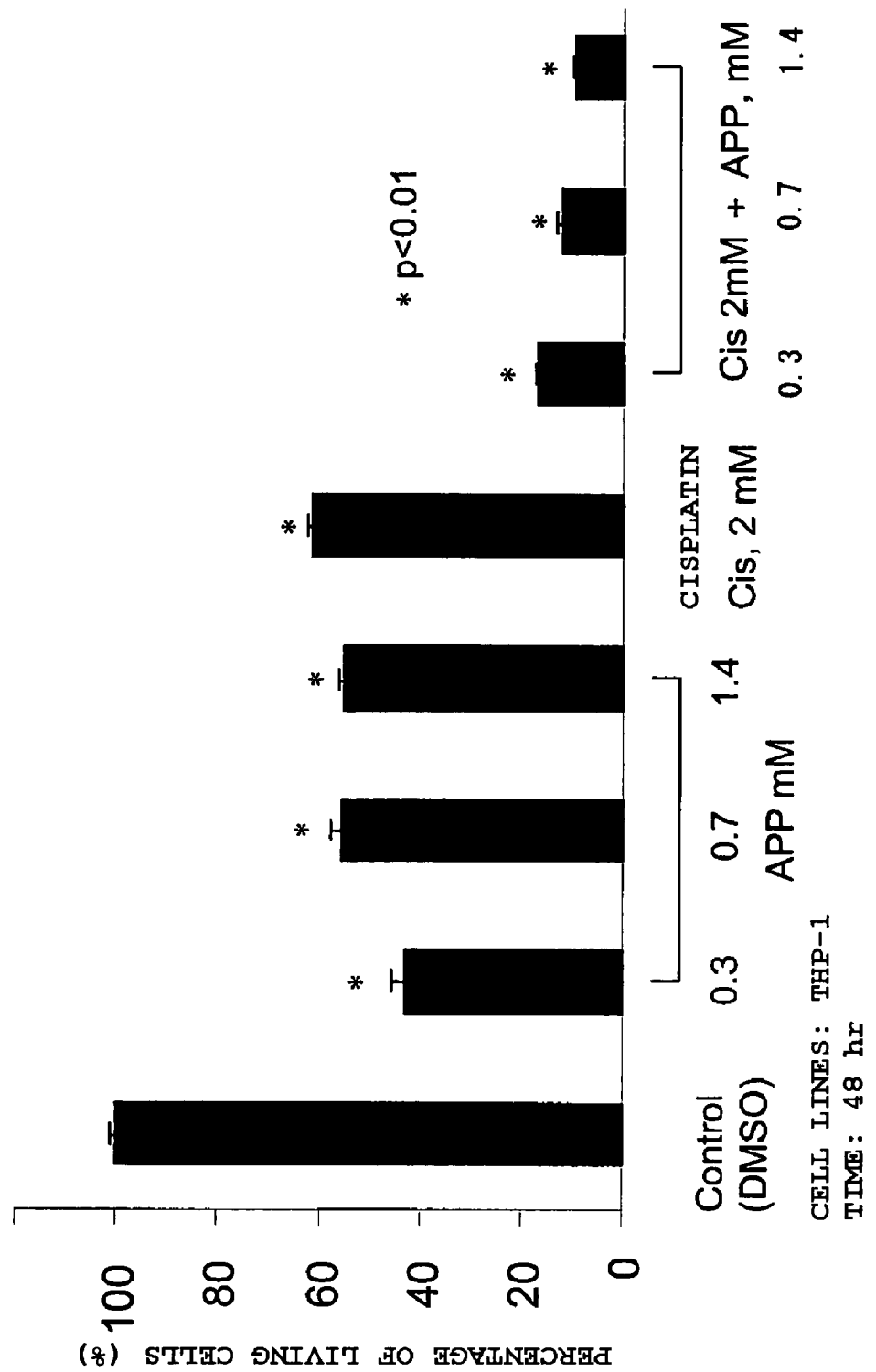
FIG. 11 shows the results of evaluation of the effect of inhibiting the growth of cells by ascopyrone P and cisplatin (Example 4).

The invention claimed is:

1. A method for treating a patient having tumor cells, which comprises administering an antitumor-effective amount of ascopyrone P to the patient thereby inducing apoptosis of the tumor cells and killing the tumor cells directly.

* * * * *